(12) United States Patent
Du et al.

(10) Patent No.: US 11,092,582 B2
(45) Date of Patent: Aug. 17, 2021

(54) DUST EMISSION FORECASTING

(71) Applicant: International Business Machines Corporation, Armonk, NY (US)

(72) Inventors: Hui Du, Beijing (CN); Yu Du, Beijing (CN); Si Huang, Beijing (CN); Yu Jia Tang, Beijing (CN); Bao Guo Xie, Beijing (CN); Meng Zhang, Beijing (CN); Xin Zhang, Lafayette, CO (US); Shuai Zhu, Beijing (CN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 934 days.

(21) Appl. No.: 15/362,225

(22) Filed: Nov. 28, 2016

(65) Prior Publication Data
US 2018/0149770 A1    May 31, 2018

(51) Int. Cl.
*G01N 33/00*    (2006.01)

(52) U.S. Cl.
CPC .............................. *G01N 33/0062* (2013.01)

(58) Field of Classification Search
CPC ......... G06Q 10/04; Y02A 90/10; G01W 1/10; G06N 20/00; G01N 33/0062
See application file for complete search history.

(56) References Cited

U.S. PATENT DOCUMENTS

| 7,242,803 B2 | 7/2007 | Miller | |
| 2007/0179640 A1* | 8/2007 | Moughler | E02F 9/2045 700/36 |
| 2014/0358442 A1 | 12/2014 | Akhlaq et al. | |
| 2016/0091474 A1* | 3/2016 | Griffon | G01N 33/0036 702/24 |

FOREIGN PATENT DOCUMENTS

| CN | 102169557 A | 8/2011 |
| CN | 203645832 U | 6/2014 |
| CN | 103927454 A | 7/2014 |

OTHER PUBLICATIONS

Badr, T. and Harion, J., "Effect of aggregate storage piles configuration on dust emissions," 2007, Atmospheric Environment 41, pp. 360-368 (Year: 2007).*

(Continued)

*Primary Examiner* — Miranda M Huang
*Assistant Examiner* — Catherine F Lee
(74) *Attorney, Agent, or Firm* — Amin, Turocy & Watson, LLP

(57) ABSTRACT

Techniques for generating dynamic dust emission risk index values via construction and use of a dynamic dust emission risk index model are provided. In one example, a computer-implemented method comprises generating, by a system operatively coupled to a processor, a dynamic dust emission risk index value based on a dynamic dust emission risk index model. The computer implemented method also includes supplying, by the system, the dynamic dust emission risk index value to an air quality model. Additionally, the computer implemented method further comprises generating, by the system, a dust emission forecast based on the air quality model.

20 Claims, 6 Drawing Sheets

(56) References Cited

OTHER PUBLICATIONS

Blight, G. E., "Wind erosion of waste impoundments in arid climates and mitigation of dust pollution," 2008, Waste Management & Research 2008: 26, pp. 523-533 (Year: 2008).*
Zheng et al., "Forecasting Fine-Grained Air Quality Based on Big Data," Aug. 2014, ACM, pp. 2267-2276 (Year: 2014).*
Wang et al., "Urban air quality and regional haze weather forecast for Yangtze River Delta region," 2012, Atmospheric Environment 58, pp. 70-83 (Year: 2012).*
Lin et al., "Long-range transport of Asian dust and air pollutants to Taiwan: observed evidence and model simulation," 2007, Atmospheric Chemistry and Physics 7, pp. 423-434 (Year: 2007).*
Guo et al., "Precipitation and air pollution at mountain and plain stations in northern China: Insights gained from observations and modeling," Apr. 2014, Journal of Geophysical Research: Atmospheres, 119, pp. 4793-4807 (Year: 2014).*
NOAA's National Weather Service Glossary, https://web.archive.org/web/20110904184812/https://forecast.weather.gov/glossary.php?word=zonal%20flow, Sep. 2011, 1 page (Year: 2011).*
Zhang, "Quantitatively monitoring dust events: better weather prediction ahead," Space Science and Engineering Center, Aug. 15, 2013, 3 pages.
Hassan, "Remotely sensing digital methods for dust storms monitoring in Iraq," Iraqi Journal of Science, 2013, vol. 54, Supplement No. 4, pp. 1219-1232.

* cited by examiner

DUST EMISSION FORECASTING

BACKGROUND

The present invention relates generally to air quality forecasting and in particular to dust emission forecasting.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later.

According to an embodiment, a computer-implemented method includes generating, by a system operatively coupled to a processor, a dynamic dust emission risk index (DDRI) value, based on a DDRI model. The method supplies the DDRI value to an air quality model and a dust emission forecast is generated based on the air quality model.

DETAILED DESCRIPTION

Figure 1:
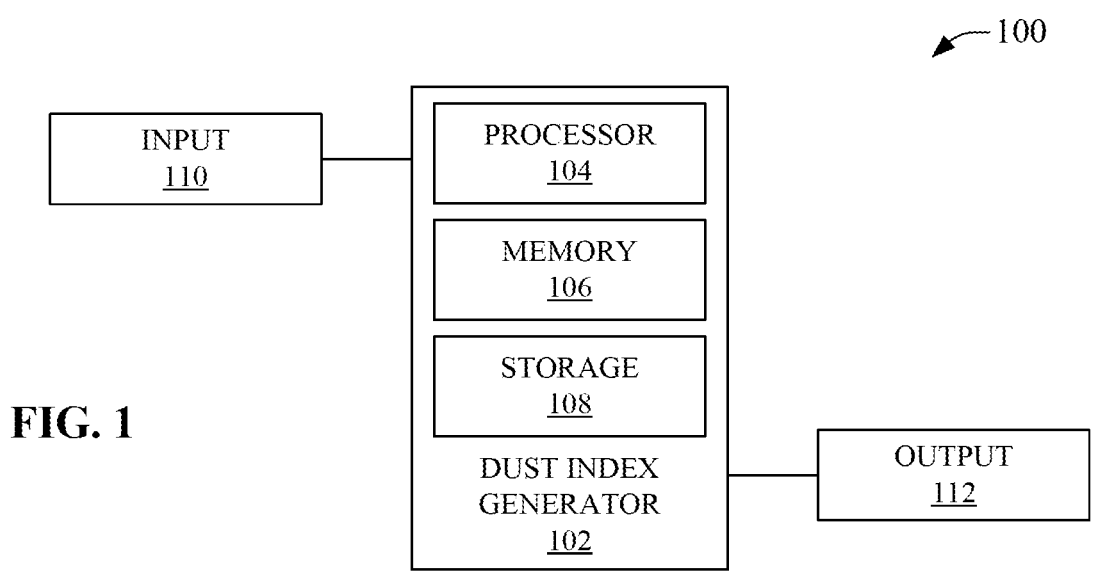
FIG. 1 illustrates a block diagram of an example, non-limiting system that facilitates generating DDRI values via construction and use of a DDRI model in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

By way of overview (and without limitation), some embodiments of the present invention are directed to one or more computer processing systems, apparatus, computer-implemented methods, and/or computer program products that facilitate efficiently and automatically generating DDRI values based on a DDRI model. By way of further overview (and without limitation), direct human participation is not required by embodiments that employ one or more computers, e.g., to: create a DDRI model based on ground information data representative of satellite remote sensing data and/or meteorological data; utilize the DDRI model to generate DDRI values; supply the DDRI values to one or more air quality models; and generate dust emission simulations/forecasts based on the air quality models. By way of further example, such creation of a DDRI model, and generation of DDRI values can involve analysis of countless thousands of geographical grid points to determine DDRI values at specific reference geographical grid points.

Moreover, computer processing systems, computer-implemented methods, apparatus and/or computer program product embodiments of the present invention employ computer hardware and/or software to solve problems that are highly technical in nature and are not abstract.

By way of overview (and without limitation), one or more aspects of systems (e.g., non-limiting system 100, depicted in FIG. 1), apparatuses or processes in accordance with the present invention can include machine-executable component(s) embodied within machine(s), e.g., computer program product comprising one or more computer readable mediums (or media) associated with one or more machines. Such component(s), when executed by the one or more machines, e.g., computer(s), computing device(s), virtual machine(s), etc. can cause the machine(s) to perform the operations described.

In various embodiments, system 100 can be any type of mechanism, machine, device, facility, apparatus, and/or instrument that includes a processor and/or is capable of effective and/or operative communication with a wired and/or wireless network. Mechanisms, machines, apparatuses, devices, facilities, and/or instrumentalities that can comprise system 100 can include (without limitation): tablet computing devices, handheld devices, server class computing machines and/or databases, laptop computers, notebook computers, desktop computers, cell phones, smart phones, consumer appliances and/or instrumentation, industrial and/or commercial devices, hand-held devices, digital assistants, multimedia Internet enabled phones, multimedia players, and the like.

Referring now to FIG. 1, a block diagram is depicted of an example, non-limiting system 100 that facilitates generating DDRI values via construction and use of a DDRI model in accordance with one or more embodiments of the present invention.

As illustrated, system 100 can include a dust index generator 102, processor 104, memory 106 and/or storage 108. In some embodiments, one or more of the dust index generator 102, processor 104, memory 106 and/or storage 108 are communicatively and/or electrically coupled to one another to perform one or more functions of system 100. In some embodiments, dust index generator 102 can receive data input 110. By way of further example, in some embodiments, the data input can be ground information data that can include one or more of: satellite remote sensing data; meteorological data received from a device comprising a network of devices associated with national metrological offices, such as, for one or more countries, a national weather service, a meteorological administration, a meteorological office, and the like; and terrain data received from devices associated with national geographic or geological survey organizations, such as a particular geological survey for a country.

Referring again to FIG. 1, Dust index generator 102, upon receiving data input 110 representing, for example, satellite remote sensing data, terrain data, and/or meteorological data, can generate a DDRI value ($I_t$) based on a DDRI model.

The DDRI value can be represented as:

$$I_t \begin{cases} = C_t(1-U_t)e^{-kQ_t}(\alpha + \beta P_t)(1-S_t)\left(1 - \frac{R_t}{R_w}\right) \\ \left(0 \le \frac{R_t}{R_w} < 0.5 \text{ mm}, 0 \le S < 0.58 \text{ mm}\right) \\ = 0 \left(\frac{R_t}{R_w} \ge 0.5 \text{ mm or } S \ge 0.58 \text{ mm}\right) \end{cases}$$

where $C_t$ represents a land use type at a defined instance in time t, such as forest type land use, agricultural type land use, urban development land use, mountainous type land use, undulating type land use, riverine type land use, desert type land use, estuarine type land use, and the like. $U_t$ represents vegetation coverage present at the defined instance in time t. The vegetation coverage can relate to whether, for instance, agricultural land use type are rice paddies, wheat fields, agricultural fields that have been left fallow, etc. Further, vegetation coverage can also include for forest type land use, whether the forest is an alpine forest, a deciduous forest, a tropical finest, and the like. $Q_t$ represents a ground specific humidity at the defined instance of time t. The ground specific humidity $Q_t$ can be the specific humidity of the soil. $S_i$ represents a snow coverage level as measured, for example, in millimeters (mm), at the defined instance in time t. $R_t$ represents an amount of precipitation (e.g., rain), measured, for instance, in millimeters (mm), that has fallen at the defined instance in time t, and $R_w$ represents a threshold value of precipitation, also measured in millimeters (mm), that typically falls in a particular location during a defined period of time (e.g., day of a week, week, fortnight, month, season (e.g., spring, summer, autumn, winter), quarter, semi-annual, annual, etc.) in which the defined instance in time t coincides. The threshold value of precipitation $R_w$ that typically falls in a particular location during a defined period of time that corresponds with the defined instance in time t can be determined from historical recorded observation data that can have been maintained by national metrological offices. $P_t$ represents an effective gradient of a windward slope, wherein the slope is measured as a gradient of the ground with respect to a horizontal plane, and $\alpha$ and $\beta$ represent weighted coefficients.

As can be observed from the foregoing, when an amount of precipitation $R_t$ (that has fallen during defined time t), divided by the threshold value of precipitation $R_w$ that typically fails during a defined period of time that corresponds to the defined instance in time t (e.g., $R_t/R_w$) is equal to or greater than 0.5 mm in the DDRI value $I_t$ is zero. Further, when the snow coverage $S_t$ at the defined instance in time t is equal to or greater than 0.58 mm, the DDRI value $I_t$ is also zero (0). Where the amount of precipitation $R_t$ that has fallen at the defined instance in time t, divided by the threshold value of precipitation $R_w$ that typically falls during a defined period of time that corresponds to the defined instance in time t (e.g., $R_t/R_w$) is equal to or greater than 0 mm and less than 0.5 mm then the DDRI value $I_t$ can be determined as a function of:

$$C_t(1-U_t)e^{-kQ_t}(\alpha + \beta P_t)(1-S_t)\left(1 - \frac{R_t}{R_w}\right)$$

The foregoing function can also be used to determine the DDRI value $I_t$ when the snow coverage $S_t$ at the defined instance in time t is equal to or greater than 0 mm and less than 0.58 mm.

Dust index generator 102 can determine the effective gradient $P_t$ by determining a wind direction, $D_{i,j,t}$, measured in radians, through use of the following $$D_{i,j,t} = \arctan \frac{V_{i,j,t}}{U_{i,j,t}}$$

wherein U is a zonal wind velocity measured, for example, in meters per second, V is a meridional wind velocity measured, for instance, in meters per second, i can represent a geographical grid point in a West-East direction within which the respective zonal and/or meridional wind velocities are measured, j can represent a geographical grid point in a South-North direction within which the respective zonal and/or meridional wind velocities are measured, and t represents the defined instance in time. A zonal wind is wind travelling in a west to east latitudinal direction and a meridional wind is wind travelling in a south to north longitudinal direction. In a rectangular coordinate system (e.g., Cartesian coordinate system), comprising an x-axis representing an eastward direction (e.g., west to east direction), and a y-axis representing a northward axis (e.g., south to north direction), a wind vector representing the zonal wind velocity U and the meridional wind velocity V can provide an indication of a magnitude of wind, such that when the zonal wind is greater than zero (0) (e.g., U>0) the wind is a west wind blowing or emanating from the west to the east, and when the meridional wind is greater than zero (0) (e.g., V>0) the wind is a south wind blowing or emanating from the south to the north.

Figure 5:
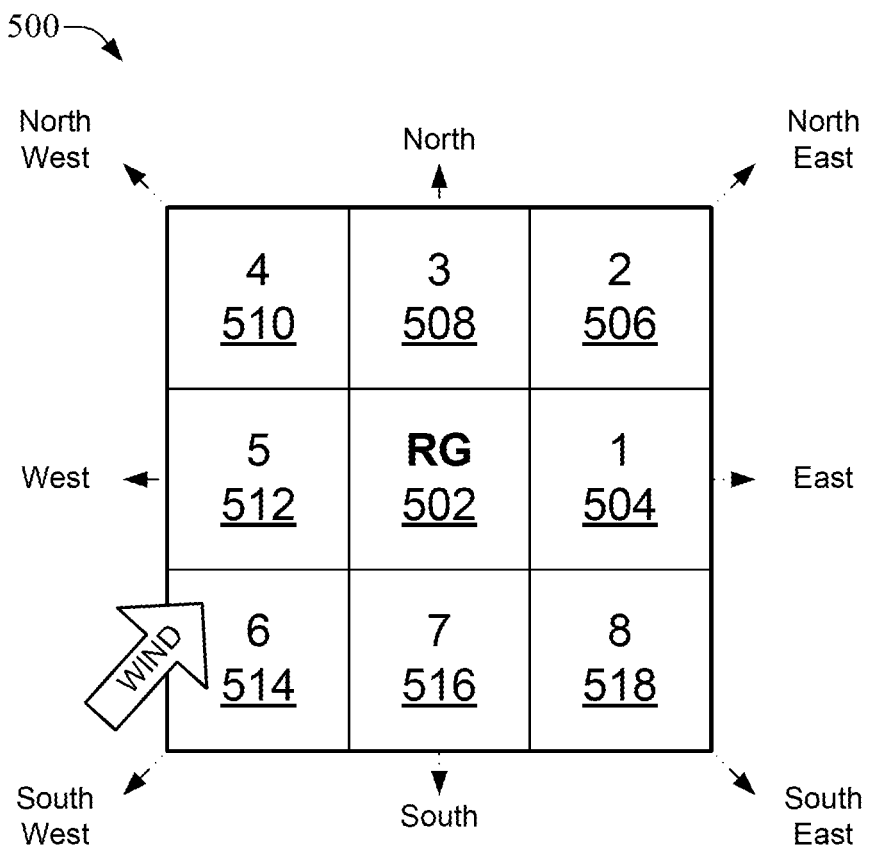
FIG. 5 illustrates an example reference grid point within adjacent geographical grids in a pattern of geographical grid adjacent to a reference grid point in accordance with one or more embodiments described herein.

With reference also now to FIG. 5, dust index generator 102 can further determine the effective gradient $P_t$ by determining the gradients in grid points adjacent to a reference grid (RG) point (e.g., i and j) of grid 500 by using the following two equations:

$$\delta H_{i,j,t}(direc) = H_{i,j,t}(direc) - H_{w_{i,j,t}}$$

$$G_{i,j,t}(direc) = \frac{\delta H_{i,j,t}(direc)}{\sqrt{\delta H_{i,j,t}(direc)^2 + \alpha Resolution^2}}$$

wherein $\delta H_{i,j,t}$ (direc) is a change in height, as measured in meters, of the terrain in an adjacent grid point (e.g., grid points 1 (504), 2 (506), 3 (508), 4 (510), 5 (512), 6 (514), 7 (516), 8 (518) that can represent, for example, the four primary compass directions (e.g., East, North, West, and South) and four ordinal compass directions (e.g., Northeast, Northwest, Southwest, and Southeast) in relation to the reference grid (RG 502) point (i, j) at an instance of time t. $\delta H_{i,j,t}$ (direc) is determined by determining a difference in the height of the terrain $H_{i,j,t}$ in the reference grid (RG 502)

point (i, j) in the direction, direc (e.g., in the direction of an adjacent grid point 1 (504), 2 (506), 3 (508), 4 (510), 5 (512), 6 (514), 7 (516), 8 (518), representing the respective primary and ordinal compass points (e.g., east, northeast, north, northwest, west, southwest, south, and southeast)) and the height $H_{w_{i,j,t}}$ at a target grid point in relation to the reference grid (RG 502) point (i, j).

For instance, in an embodiment the height of the terrain $H_{i,j,t}$ in reference grid (RG) point (i, j) in direction, direc, pointing to the north-east quadrant (e.g., pointing toward grid point 2 (506)) can be 100 meters, and the height of the terrain $H_{w_{i,j,t}}$ in target grid point 2 (506) can be −250 meters thus the difference in height $\delta H_{i,j,t}$ (direc) pointing to the northeast quadrant (e.g., towards grid point 2 (506)) would be (100−250)=350 meters. In a further embodiment, the height of the terrain in the south-west quadrant (e.g., grid point 6 (514)) can be 190 meters and the, thus the difference in height $\delta H_{i,j,t}$ (direc) with respect to the reference grid (RG 502) point (i,j) point in the southwest quadrant would be (100−190)=90 meters.

The gradient, $G_{i,j,t}$ with respect to the reference grid (RG 502) point (i, j) in a direction direc of another grid point (e.g., in the direction of adjacent grid points 1 (504), 2 (506), 3 (508), 4 (510), 5 (512), 6 (514), 7 (516), or 8 (518), representing the respective primary and/or ordinal compass points (e.g., east, northeast, north, northwest, west, southwest, south, and southeast)) at an instance of time t, can be determined by dividing the change in height ($\delta_{i,j,t}$ (direc)), as measured in meters, between the height of the terrain in the reference grid (RG) point (i, j) in comparison with the height of the terrain in a particular adjacent grid point (e.g., grid points 1 (504), 2 (506), 3 (508), 4 (510), 5 (512), 6 (514), 7 (516), 8 (518)) at time instance t, with the square root of the sum of the square of the change in height $\delta H_{i,j,t}$ (direc), between the height of the terrain in the reference grid (RG) point (i, j) in comparison with the height of the terrain in the particular adjacent grid point (e.g., grid points 1 (504), 2 (506), 3 (508), 4 (510), 5 (512), 6 (514), 7 (516), 8 (518)) at time instance t and the square of a square of a resolution value (Resolution) multiplied by a weighting coefficient ($\alpha$). The resolution value (Resolution) is a variable that accounts for differences between resolutions supplied by one or more various air quality forecasting model(s) (e.g., air quality component 212). In some embodiments, one or more air quality forecasting model from a group of air quality models comprising congestion mitigation and a quality improvement (CMAQ), nested air quality prediction modeling system (NAQPMS), and the like) and the resolution generated by the disclosed DDRI model can be used. An example calculation of a Resolution value will be described in more detail below.

Dust index generator 102 can further determine the effective gradient for a windward slope through use of the following equations:

$$\alpha_{i,j,t} = \frac{\min_1 (|D_{direc=1,2,\ldots 8} - D_{i,j,t}|)}{\frac{\pi}{4}}$$

$$\beta_{i,j,t} = \frac{\min_2 (|D_{direc=1,2,\ldots 8} - D_{i,j,t}|)}{\frac{\pi}{4}}$$

wherein the equations $\alpha_{i,j,t}$ and $\alpha_{i,j,t}$ can be utilized to identify, with regard to the reference grid (RG) point (i, j), at least two adjacent grids within which the respective wind directions are substantially congruent with the wind direction as measured at reference grid (RG) point (i, j). Further, the effective gradient $P_{i,j,t}$ for the windward slope is also determined by using the following equation:

$$P_{i,j,t}=(1-\alpha_{i,j,t})G_{i,j,t}(\text{direc}_{min1})+(1-\beta_{i,j,t})G_{i,j,t}(\text{direc}_{min2})$$

wherein $(1-\alpha_{i,j,t})$ and $(1-\beta_{i,j,t})$ represent weighted coefficients, $G_{i,j,t}$ ($\text{direc}_{min1}$), and $G_{i,j,t}$ ($\text{direc}_{min2}$) respectively represent gradients with respect to the at least two adjacent grids within which the wind directions are substantially correspondent with the wind direction as measured from the perspective of reference grid (RG) point (i, j).

Dust index generator 102, because of resolution disparities between the resolutions generated and output 112 by the DDRI model developed and used by dust index generator 102 and existing air quality models such as: nested air quality prediction modeling system (NAQPMS), weather research and forecasting coupled with chemistry (WRF-Chem) model, congestion mitigation and air quality (CMAQ) improvement model, and the like, can resolve the differences between the finer granularities produced and generated by dust index generator 102 and the courser granularities utilized by existing air quality models through interpolation. For instance, where it is determined that the resolution (Resolution) of the output 112 generated by the DDRI model developed and used by dust index generator 102 at a grid point (x, y) is greater than the resolution ($r_k$) utilized by existing air quality models at a corresponding grid point ($x_k$, $y_k$) (e.g., $r_k \leq$ Resolution), then the following equations can be used to resolve differences in resolution:

$$r_k = \sqrt{(x-x_k)^2 + (y-y_k)^2}$$

$$f(x,y) = f_k(r_k = 0)$$

$$f(x,y) = \frac{\sum_{k=1}^{N} \frac{f_k}{r_k^2}}{\sum_{k=1}^{N} \frac{1}{r_k^2}}$$

Figure 2:
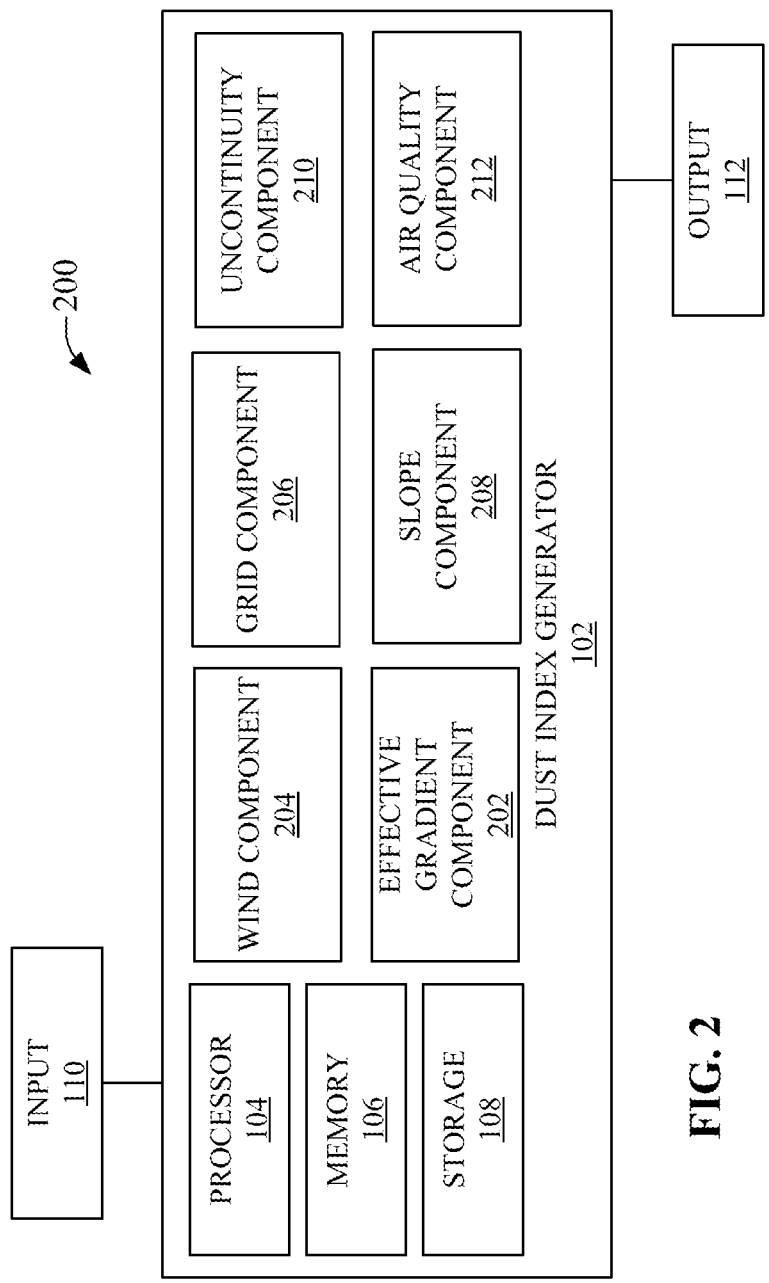
FIG. 2 illustrates another block diagram of an example, non-limiting system that facilitates generating DDRI values via construction and use of a DDRI model in accordance with one or more embodiments described herein.

FIG. 2 illustrates another block diagram of an example, non-limiting system that facilitates generating DDRI values via construction and use of a DDRI model in accordance with one or more embodiments described herein. Repetitive description of like elements employed in other embodiments described herein is omitted for sake of brevity.

Non-limiting system 200 can include one or more of the components and/or functionality of system 100, and vice versa. As illustrated, dust index generator 102 system 200 can include effective gradient component 202 that can receive ground information data representing, for instance, satellite remote sensing data, terrain data, and/or meteorological data. Effective gradient component 202 on receiving the ground information data can generate a DDRI value ($I_t$) based on DDRI model represented as:

$$I_t \begin{cases} = C_t(1-U_t)e^{-kQ_t}(\alpha+\beta P_t)(1-S_t)\left(1-\frac{R_t}{R_w}\right) \\ \left(0 \leq \frac{R_t}{R_w} < 0.5 \text{ mm}, 0 \leq S < 0.58 \text{ mm}\right) \\ = 0\left(\frac{R_t}{R_w} \geq 0.5 \text{ mm or } S \geq 0.58 \text{ mm}\right) \end{cases}$$

where $C_t$ is a land use type, such as forest type land use, agricultural type land use, urban development land use, mountainous type land use, undulating type land use, riverine type land use, desert type land use, estuarine type land use, and the like. $U_t$ represents vegetation coverage present at an instance in time t, such as agricultural land use (e.g., wheat fields, agricultural fields that have been left fallow, etc.), forest type land use (e.g., whether the forest is an alpine forest, a deciduous forest, a tropical forest, and the like). $Q_t$ represents a ground specific humidity of the soil as measured in millimeters at an instance of time. $S_t$ represents a snow coverage level as measured in millimeters (mm), at the defined instance in time t. $R_t$ represents an amount of precipitation (e.g., rain), measured, for instance, in millimeters (mm), that has fallen at the defined instance in time t, and $R_w$ represents a threshold value of precipitation, also measured in millimeters (mm), that typically falls in a particular location during a defined period of time (e.g., day of a week, week, fortnight, month, season (e.g., spring, summer, autumn, winter), quarter, semi-annual, annual, etc.) in which the defined instance in time t coincides. The threshold value of precipitation $R_w$ that typically falls in a particular location during a defined period of time that corresponds with the defined instance in time t can be determined from historical recorded observation data that can have been maintained by national metrological offices. $P_t$ represents an effective gradient of a windward slope, wherein the slope is measured as a gradient of the ground with respect to a horizontal plane, and $\alpha$ and $\beta$ represent weighted coefficients.

As illustrated, dust index generator 102 can include wind component 204 that in conjunction with dust index generator 102 and effective gradient component 202 can determine a wind direction $D_{i,j,t}$ measured in radians. The wind direction, $D_{i,j,t}$, can be determined through use of the following equation;

$$D_{i,j,k} = \arctan \frac{V_{i,j,t}}{U_{i,j,t}}$$

where U represents a zonal wind velocity measured, for example, in meters per second, V represents a meridional wind velocity measured, for instance, in meters per second, i denotes a geographical grid point in a West-East direction within which the respective zonal and/or meridional wind velocities are measured, j denotes a geographical grid point in a South-North direction within which the respective zonal and/or meridional wind velocities are measured, and t represents the defined instance in time.

Figure 4:
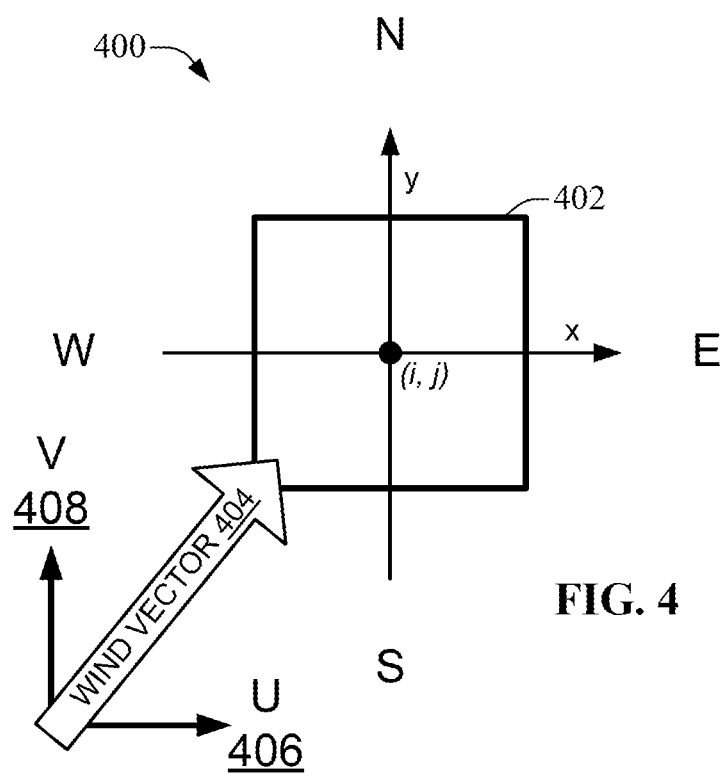
FIG. 4 illustrates an example of a rectangular coordinate system representation of a wind vector representing the zonal wind velocity and a meridional wind velocity in accordance with one or more embodiments described herein.

Referring now to FIG. 4, an example is depicted of a rectangular coordinate system representation of a wind vector representing the zonal wind velocity and a meridional wind velocity in accordance with one or more embodiments of the present invention. As depicted, a rectangular coordinate system 400, such as a Cartesian coordinate system, can include an x-axis that corresponds to an eastward direction (e.g. a zonal wind blowing from west to east), a y-axis that corresponds to a northward direction (e.g., a meridional wind blowing from the south to the north), and a grid point 402 that can represent a geographical grid point (i, j) in a respective West-East direction and a South-North direction within the rectangular coordinate system. Also illustrated is an exemplary wind vector 404 representing a wind emanating from the southwest quadrant, the magnitude of wind vector 404 corresponds to the magnitudes of the zonal wind velocity U (406) and the meridional wind velocity V (408) measured at the geographical grid point (i, j) at a particular defined instance of time t.

As further illustrated in FIG. 2, dust index generator 102 can include grid component 206 that in conjunction with wind component 204 and effective gradient component 202 can determine the gradients in each grid point adjacent to a reference grid (RG) point (see FIG. 10, RG 502) by using the following equations:

$$\delta H_{i,j,t}(direc) = H_{i,j,t}(direc) - H_{w_{i,j,t}}$$

$$G_{i,j,t}(direc) = \frac{\delta H_{i,j,t}(direc)}{\sqrt{\delta H_{i,j,t}(direc)^2 + \alpha Resolution^2}}$$

wherein $\delta H_{i,j,t}$ (direc) is a change in height, as measured in meters, of the terrain in an adjacent grid point (e.g., FIG. 5 grid points 1 (504), 2 (506), 3 (508), 4 (510), 5 (512), 6 (514), 7 (516), 8 (518)) in relation to the reference grid (RG) point at an instance of time t. $\delta H_{i,j,t}$ (direc) is determined by determining a difference in the height of the terrain $H_{i,j,t}$ in the reference grid (RG) point in the direction, direc (e.g., in the direction of an adjacent grid point 1 (504), 2 (506), 3 (508), 4 (510), 5 (512), 6 (514), 7 (516), or 8 (518)) and the height $H_{w_{i,j,t}}$ at a target grid point in relation to the reference grid (RG) point.

The gradient, $G_{i,j,t}$ with respect to the reference grid (RG) point in a direction three of other grid points (e.g., in the direction of adjacent grid points 1 (504), 2 (506), 3 (508), 4 (510), 5 (512), 6 (514), 7 (516), or 8 (518)) at an instance of time t, can be determined by dividing the change in height ($\delta H_{i,j,t}$ (direc)), as measured in meters, between the height of the terrain in the reference grid (RG) point in comparison with the height of the terrain in a particular adjacent grid point (e.g., grid points 1 (504), 2 (506), 3 (508), 4 (510), 5 (512), 6 (514), 7 (516), 8 (518)) at time instance t, with the square root of the sum of the square of the change in height ($\delta H_{i,j,t}$ (direc), between the height of the terrain in the reference grid (RG) point in comparison with the height of the terrain in the particular adjacent grid point (e.g., grid points 1 (504), 2 (506), 3 (508), 4 (510), 5 (512), 6 (514), 7 (516), 8 (518)) at time instance t and the square of a square of a resolution value (Resolution) multiplied by a weighting coefficient ($\alpha$). The resolution value (Resolution) is a variable necessary to account for differences between resolutions supplied by current air quality forecasting models.

As also illustrated in FIG. 2, dust index generator 102 can include slope component 208 that can operate in conjunction with grid component 206, wind component 204, and effective gradient component 202 to determine the effective gradient for a windward slope through the use of the following equations:

$$\alpha_{i,j,t} = \frac{\min_1(|D_{direc=1,2,\ldots 8} - D_{i,j,t}|)}{\frac{\pi}{4}}$$

$$\beta_{i,j,t} = \frac{\min_2(|D_{direc=1,2,\ldots 8} - D_{i,j,t}|)}{\frac{\pi}{4}}$$

wherein the respective equations for the determination of $\alpha_{i,j,t}$ and $\beta_{i,j,t}$ identify, with regard to the reference grid (RG) point (i, j), the at least two adjacent grids within which the respective wind directions are substantially correspondent with the wind direction as measured at reference grid (RG) point (i, j). Further, the effective gradient $P_{i,j,t}$ for the windward slope is also determined by slope component 208 by using the following equation:

$$P_{i,j,t} = (1-\alpha_{i,j,t})G_{i,j,t}(direc_{min_1}) + (1-\beta_{i,j,t})G_{i,j,t}(direc_{min_2})$$

wherein $(1-\alpha_{i,j,t})$ and $(1-\beta_{i,j,t})$ represent weighted coefficients, $G_{i,j,t}$ ($direc_{min_1}$), and $G_{i,j,t}$ ($direc_{min_2}$) respectively represent gradients with respect to at least two adjacent grid points for which the wind directions are substantially equivalent to the wind direction as measured from the perspective of reference grid (RG) point (i, j).

Additionally as illustrated in FIG. 2, dust index generator 102 can also include uncontinuity component 210 that, in conjunction with slope component 208, grid component 206, wind component 204, and effective gradient component 202 can rectify resolution disparities between resolutions generated and output 112 by the DDRI model developed and used by dust index generator 102 and existing air quality models (e.g., air quality component 212) such as: the nested air quality prediction modeling system (NAQPMS), the weather research and forecasting coupled with chemistry (WRF-Chem) model, the congestion mitigation and air quality (CMAQ) improvement model, and the like. In order to resolve these resolution disparities, uncontinuity component 210 can resolve the differences between the finer granularities output 112 by the DDRI model as DDRI values (I) and the courser granularities utilized by existing air quality models through interpolation. For example, where it is determined by uncontinuity component 210 that the resolution (Resolution) of the output 112 generated by the DDRI model at a grid point (x, y) is greater than the resolution ($r_k$) utilized by existing air quality models at a corresponding grid point ($x_k$, $y_k$) (e.g., $r_k \leq$ Resolution), then the following equations can be used by uncontinuity component 210 to resolve the discrepancies in resolution:

$$r_k = \sqrt{(x-x_k)^2 + (y-y_k)^2}$$

$$f(x, y) = f_k(r_k = 0)$$

$$f(x, y) = \frac{\sum_{k=1}^{N} \frac{f_k}{r_k^2}}{\sum_{k=1}^{N} \frac{1}{r_k^2}}$$

Some of the foregoing processes performed may be performed by specialized computers for carrying out defined tasks related to generating DDRI values via construction and use of a DDRI model. The subject computer processing systems, methods, apparatuses and/or computer program products can be employed to solve new problems that arise through advancements in technology, computer networks, the Internet and the like. The subject computer processing systems, methods, apparatuses and/or computer program products can provide technical improvements to automated performance of generating DDRI values via construction and use of a DDRI model by improving processing efficiency among processing components in generating DDRI values via construction and use of a DDRI model, reducing delay in processing performed by the processing components, and improving the accuracy in which the processing systems perform generating DDRI values via construction and use of a DDRI model.

Figure 3:
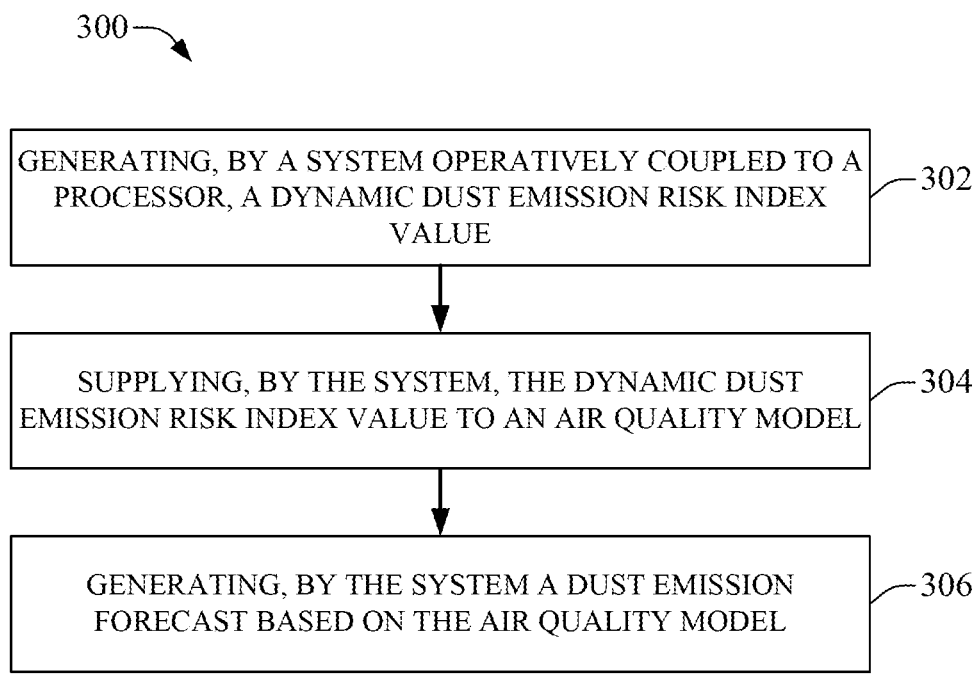
FIG. 3 illustrates a flow diagram of an example, non-limiting computer-implemented method facilitates generating DDRI values via construction and use of a DDRI model in accordance with one or more embodiments described herein.

FIG. 3 illustrates a flow diagram of an example, non-limiting computer-implemented method 300 that facilitates generating DDRI values via construction and use of a DDRI model in accordance with one or more embodiments described herein. Repetitive description of like elements employed in other embodiments described herein is omitted for sake of brevity.

At 302, a system operatively coupled to a processor (e.g., dust index generator 102 of system 200) can through use of effective gradient component 202, wind component 204, grid component 206, and slope component 208 generate a DDRI value. The DDRI value can be based on received meteorological data and satellite data and a DDRI model that can be represented as:

$$I_t \begin{cases} = C_t(1-U_t)e^{-kQ_t}(\alpha + \beta P_t)(1-S_t)\left(1-\frac{R_t}{R_w}\right) \\ \left(0 \leq \frac{R_t}{R_w} < 0.5 \text{ mm}, 0 \leq S < 0.58 \text{ mm}\right) \\ = 0\left(\frac{R_t}{R_w} \geq 0.5 \text{ mm or } S \geq 0.58 \text{ mm}\right) \end{cases}$$

At 304, the system 200, using uncontinuity component 210 can supply the DDRI value ($I_t$) to an air quality model, such as: nested air quality prediction modeling system (NAQPMS), weather research and forecasting coupled with chemistry (WRF-Chem) model, congestion mitigation and air quality (CMAQ) improvement model, and the like. At 306 a dust emission forecast can be generated by for example, dust index generator 102, based on the air quality model.

In an additional and/or alternative embodiment at 306, rather than generating a dust emission forecast, a dust emission simulation can be generated by, for example, dust index generator 102, based on the air quality model, such as, air quality component 212, (e.g., nested air quality prediction modeling system (NAQPMS), weather research and forecasting coupled with chemistry (WRF-Chem) model, congestion mitigation and air quality (CMAQ) improvement model, and the like).

For simplicity of explanation, the computer-implemented methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts can be required to implement the computer-implemented methodologies in accordance with the disclosed subject matter. In addition, those skilled in the art will understand and appreciate that the computer-implemented methodologies could alternatively be represented as a series of interrelated states via a state diagram or events. Additionally, it should be further appreciated that the computer-implemented methodologies disclosed hereinafter and throughout this specification are capable of being stored on an article of manufacture to facilitate transporting and transferring such computer-implemented methodologies to computers. The term article of manufacture, as used herein, is intended to encompass a computer program accessible from any computer-readable device or storage media.

Figure 6:
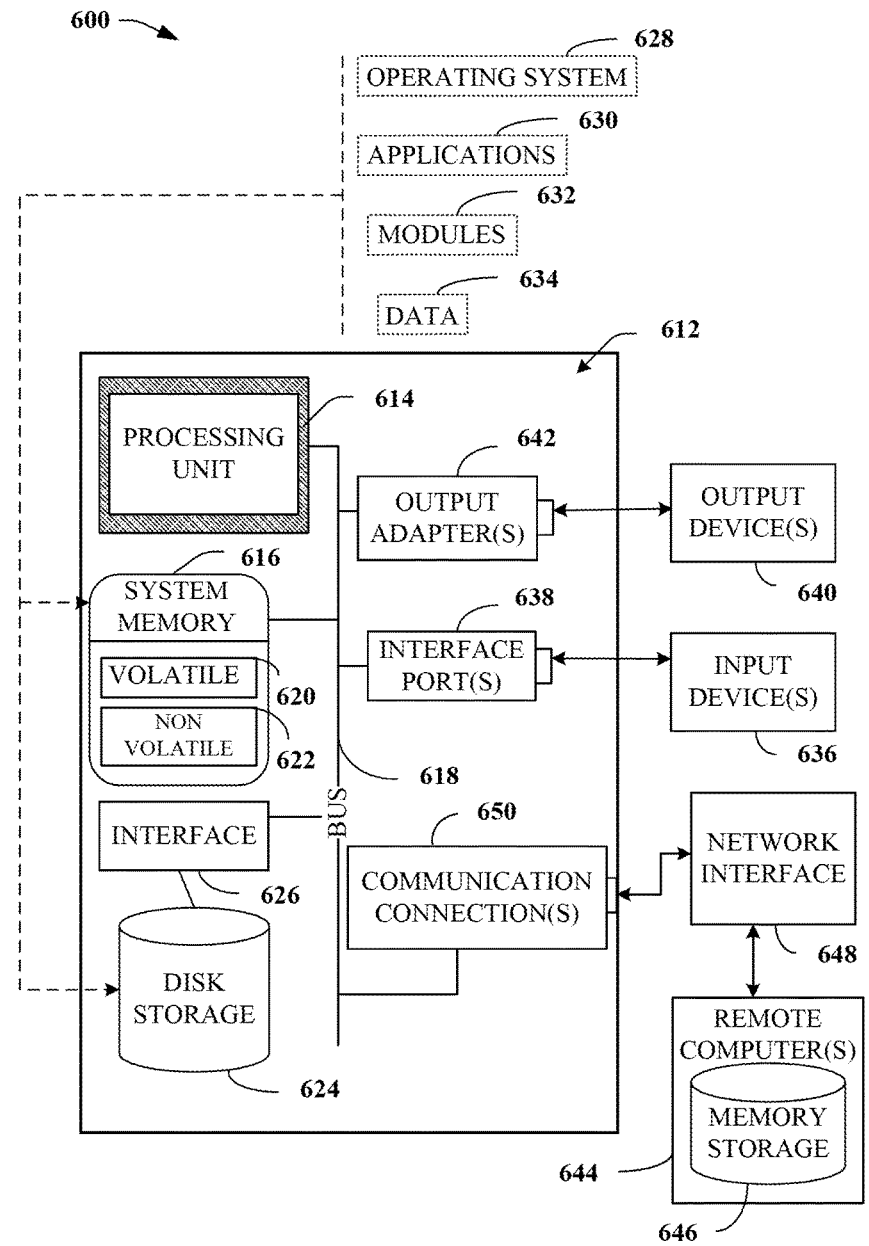
FIG. 6 illustrates a block diagram of an example, non-limiting operating environment in which one or more embodiments described herein can be facilitated.

The following discussion, with reference to FIG. 6, is intended to provide a general description of a suitable environment in which various aspects of the present invention can be implemented.

FIG. 6 illustrates a block diagram of an example, non-limiting operating environment in which one or more embodiments described herein can be facilitated. Repetitive description of like elements employed in other embodiments described herein is omitted for sake of brevity. As depicted, a suitable operating environment 600 for implementing various aspects of this invention can include a computer 612. The computer 612 can include a processing unit 614, a system memory 616, and a system bus 618. The system bus 618 communicatively couples system components, including but not limited to, system memory 616 to the processing unit 614. The processing unit 614 can be any of various available processors. Dual microprocessors and other multiprocessor architectures also can be employed as the processing unit 614. The system bus 618 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI). The system memory 616 can include volatile memory 620 and nonvolatile memory 622. The basic input/output system (BIOS), containing the basic routines to transfer information between elements within the computer 612, such as during start-up, is stored in nonvolatile memory 622. By way of illustration, and not limitation, nonvolatile memory 622 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 620 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 612 can also include removable/non-removable, volatile/non-volatile computer storage media, for example, disk storage 624. Examples of disk storage 624 include, but are not limited to, devices like a magnetic disk drive, floppy disk drive, tape drive, Jaz drive, Zip drive, LS-100 drive, flash memory card, or memory stick. The disk storage 624 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 624 to the system bus 618, a removable or non-removable interface is typically used, such as interface 626. FIG. 6 also depicts software that acts as an intermediary between users and the basic computer resources described in the suitable operating environment 600. Such software can also include, for example, an operating system 628. Operating system 628, which can be stored on disk storage 624, acts to control and allocate resources of the computer 612. System applications 630 take advantage of the management of resources by operating system 628 through program modules 632 and program data 634, e.g., stored either in system memory 616 or on disk storage 624. For instance, program modules 632 and program data 634 can comprise modules and data for the execution of instructions associated with generating a dynamic dust emission risk index value based on a dynamic dust emission risk index model, supplying the dynamic dust emission risk index value to an air quality model, and generating a dust emission forecast based on the air quality model. For example, the foregoing instructions can be performed by effective gradient component 202, wind component 204, grid component 206, slope component 208, and/or unconformity component 602. It is to be appreciated that this invention can be implemented with various operating systems or combinations of operating systems. A user enters commands or information into the computer 612 through input device(s) 636. Input devices 636 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 614 through the system bus 618 via interface port(s) 638. Interface port(s) 638 include, for example, a serial port, a parallel port, a game port, and a universal serial bus (USB). Output device(s) 640 use some of the same type of ports as input device(s) 636. Thus, for example, a USB port can be used to provide input to computer 612, and to output information from computer 612 to an output device 640. Output adapter 642 is provided to illustrate that there are some output devices 640 like monitors, speakers, and printers, among other output devices 640, which require special adapters. The output adapters 642 include, by way of illustration and not limitation, video and sound cards that provide a means of connection between the output device 640 and the system bus 618. It should be noted that other devices and/or systems of devices provide both input and output capabilities such as remote computer(s) 644.

Computer 612 can operate in a networked environment using logical connections to one or more remote computers, such as remote computer(s) 644. The remote computer(s) 644 can be a computer, a server, a router, a network PC, a workstation, a microprocessor based appliance, a peer device or other common network node and the like, and typically can also include many or all of the elements described relative to computer 612. For purposes of brevity, only a memory storage device 646 is illustrated with remote computer(s) 644. Remote computer(s) 644 is logically connected to computer 612 through a network interface 648 and then physically connected via communication connection 650. Network interface 648 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 650 refers to the hardware/software employed to connect the network interface 648 to the system bus 618. While communication connection 650 is shown for illustrative clarity inside computer 612, it can also be external to computer 612. The hardware/software for connection to the network interface 648 can also include, for exemplary purposes only, internal and external technologies such as, modems including regular telephone grade modems, cable modems and DSL modems, ISDN adapters, and Ethernet cards.

Embodiments of the present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various aspects of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this invention also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this invention can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and number-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this invention are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transition word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, comprising:
   generating, by a system operatively coupled to a processor, a dynamic dust emission risk index value based on a dynamic dust emission risk index model and an effective gradient of a windward slope of land in a defined area, wherein the effective gradient is determined based on a first function of:
      a wind direction determined by a second function of a zonal wind velocity at a reference grid point of a grid defining the defined area and a meridional wind velocity at the reference grid point in the defined area,
      at least two grid points of the grid that are determined by a third function to be adjacent to the reference grid and have respective wind directions congruent to the wind direction, and
      respective gradients in the at least two grid points as determined by a fourth function of respective changes in heights of the land in the grid points;
   supplying, by the system, the dynamic dust emission risk index value to an air quality model; and
   generating, by the system, a dust emission forecast based on the air quality model.

2. The computer implemented method of claim 1, wherein the dynamic dust emission risk index model is created based on ground information data representing satellite remote sensing data.

3. The computer-implemented method of claim 2, wherein the ground information data comprises land use type data selected from a grouping consisting of: vegetation coverage data and ground specific humidity data.

4. The computer-implemented method of claim 1, wherein the dynamic dust emission risk index value is further based on ground information data selected from a group consisting of: vegetation coverage data, land use type data, snow coverage data, meteorological data, precipitation data, wind direction data, and effective gradient data.

5. The computer-implemented method of claim 1, wherein the air quality model is selected from a group consisting of: a nested air quality prediction modeling system; a weather research and forecasting (coupled with chemistry) model; and a congestion mitigation and air quality improvement model.

6. The computer implemented method of claim 1, wherein the zonal wind velocity is associated with wind travelling in a west to east latitudinal direction, and the meridional wind velocity is associated with wind travelling in a south to north longitudinal direction.

7. A computer program product comprising a computer readable storage medium having program instructions embodied therewith, the program instructions executable by a processing component to cause the processing component to:
   generate, by the processing component, based on a dynamic dust emission risk index model and an effective gradient of a windward slope of land in a defined area, a dynamic dust emission risk index value, wherein the effective gradient is determined based on a first function of:
      a wind direction determined by a second function of a zonal wind velocity at a reference grid point of a grid defining the defined area and a meridional wind velocity at the reference grid point in the defined area,
      at least two grid points of the grid that are determined by a third function to be adjacent to the reference grid and have respective wind directions congruent to the wind direction, and
      respective gradients in the at least two grid points as determined by a fourth function of respective changes in heights of the land in the grid points;
   supply, by the processing component, the dynamic dust emission risk index value to an air quality model; and
   generate, by the processing component, based on the air quality model, a dust emission forecast.

8. The computer program product of claim 7, wherein the dynamic dust emission risk index value is further based on ground information data selected from a group consisting of: vegetation coverage data, land use type data, snow coverage data, meteorological data, precipitation data, wind direction data, and effective gradient data.

9. The computer program product of claim 8, wherein the air quality model is selected from a group consisting of: a nested air quality prediction modeling system; a weather research and forecasting (coupled with chemistry) model; and a congestion mitigation and air quality improvement model.

10. The computer program product of claim 8, wherein the respective changes in heights are in relation to the reference grid point.

11. The computer program product of claim 7, wherein the zonal wind velocity is associated with wind travelling in a west to east latitudinal direction, and the meridional wind velocity is associated with wind travelling in a south to north longitudinal direction.

12. The computer program product of claim 7, wherein the program instructions further cause the processor to determine a resolution value that adjusts the dynamic dust emission risk index value from a first resolution value used by the dynamic dust emission index model to a second resolution value, wherein the first resolution value is used by the dynamic dust emission index model and the second resolution value is used by the air quality model.

13. A system for generating a dust emission forecast, comprising:
   a processor;
   a memory operatively coupled to the processor, wherein the memory stores program instructions, which when executed by the processor, cause the processor to:
      generate a dynamic dust emission risk index value based on a dynamic dust emission risk index model and an effective gradient of a windward slope of land in a defined area, wherein the effective gradient is determined based on a first function of:
         a wind direction determined by a second function of a zonal wind velocity at a reference grid point of a grid defining the defined area and a meridional wind velocity at the reference grid point in the defined area, at least two grid points of the grid that are determined by a third function to be adjacent to the reference grid and have respective wind directions congruent to the wind direction, and respective gradients in the at least two grid points as determined by a fourth function of respective changes in heights of the land in the grid points;

supply the dynamic dust emission risk index value to an air quality model; and generate a dust emission forecast based on the air quality model.

14. The system of claim 13, wherein the dynamic dust emission risk index model is created based on ground information data representing satellite remote sensing data.

15. The system of claim 14, wherein the ground information data comprises land use type data selected from a grouping consisting of: vegetation coverage data and ground specific humidity data.

16. The system of claim 13, wherein the dynamic dust emission risk index value is further based on ground information data selected from a group consisting of: vegetation coverage data, land use type data, snow coverage data, meteorological data, precipitation data, wind direction data, and effective gradient data.

17. The system of claim 13, wherein the air quality model is selected from a group consisting of: a nested air quality prediction modeling system; a weather research and forecasting (coupled with chemistry) model; and a congestion mitigation and air quality improvement model.

18. The system of claim 16, wherein respective changes in heights are in relation to the reference grid point.

19. The system of claim 13, wherein the zonal wind velocity is associated with wind travelling in a west to east latitudinal direction, and the meridional wind velocity is associated with wind travelling in a south to north longitudinal direction.

20. The system of claim 13, wherein the program instructions further cause the processor to determine a resolution value that adjusts the dynamic dust emission risk index value from a first resolution value used by the dynamic dust emission index model to a second resolution value, wherein the first resolution value is used by the dynamic dust emission index model and the second resolution value is used by the air quality model.

* * * * *